United States Patent
Narang et al.

(10) Patent No.: US 6,183,593 B1
(45) Date of Patent: Feb. 6, 2001

(54) 1,1-DISUBSTITUTED ETHYLENE ADHESIVE COMPOSITIONS CONTAINING POLYDIMETHYLSILOXANE

(75) Inventors: Upvan Narang; William S. C. Nicholson, both of Raleigh, NC (US)

(73) Assignee: Closure Medical Corporation, Raleigh, NC (US)

( * ) Notice: Under 35 U.S.C. 154(b), the term of this patent shall be extended for 0 days.

(21) Appl. No.: 09/471,392

(22) Filed: Dec. 23, 1999

(51) Int. Cl.⁷ ............... C09J 183/04; A61K 7/48
(52) U.S. Cl. ............................. 156/327; 156/329
(58) Field of Search .................... 156/327, 329; 424/78.02, 78.06, 78.03; 422/21, 22, 20, 23, 24

(56) References Cited

U.S. PATENT DOCUMENTS

| | | |
|---|---|---|
| Re. 32,889 | 3/1989 | Litke ..................... 523/212 |
| 2,721,858 | 11/1955 | Joyner et al. ............. 260/67 |
| 3,254,111 | 5/1966 | Hawkins et al. .......... 260/465.4 |
| 3,554,990 | 1/1971 | Quinn et al. ............ 260/88.7 |
| 3,940,362 | 2/1976 | Overhults ............... 260/42.16 |
| 3,995,641 | 12/1976 | Kronenthal et al. ....... 128/335 |
| 4,180,911 | 1/1980 | Bullock .................. 433/9 |
| 4,313,865 | 2/1982 | Teramoto et al. ......... 260/31.4 R |
| 4,364,876 | 12/1982 | Kimura et al. ........... 260/465.4 |
| 4,477,607 | 10/1984 | Litke ..................... 523/212 |
| 4,533,422 | 8/1985 | Litke ..................... 156/307.3 |
| 4,560,723 | 12/1985 | Millet et al. ............. 524/486 |
| 4,636,539 | 1/1987 | Harris et al. ............ 523/214 |
| 4,650,826 | 3/1987 | Waniczek et al. ......... 524/730 |
| 4,686,247 | 8/1987 | Yosida ................... 523/213 |
| 4,705,836 | 11/1987 | Ohtsuka et al. .......... 526/318.1 |
| 4,713,405 | 12/1987 | Koga et al. ............. 523/212 |
| 4,720,513 | 1/1988 | Kameyama et al. ....... 523/203 |
| 4,764,545 | 8/1988 | Yosida ................... 523/212 |
| 4,837,260 | 6/1989 | Sato et al. .............. 524/261 |
| 4,906,317 | 3/1990 | Lin ...................... 156/307.3 |
| 5,140,084 | 8/1992 | Mikuni et al. ........... 326/279 |
| 5,214,093 | 5/1993 | Nell et al. .............. 524/506 |
| 5,248,708 | 9/1993 | Uemura et al. .......... 523/212 |
| 5,328,687 * | 7/1994 | Leung et al. ........... 424/78.35 |
| 5,373,035 | 12/1994 | Uemura et al. .......... 523/212 |
| 5,386,047 | 1/1995 | Nakos et al. ............ 556/416 |
| 5,514,371 * | 5/1996 | Leung et al. ........... 424/78.35 |
| 5,514,372 | 5/1996 | Leung et al. ........... 424/78.35 |
| 5,575,997 | 11/1996 | Leung et al. ........... 424/78.35 |
| 5,582,834 | 12/1996 | Leung et al. ........... 424/426 |
| 5,624,669 | 4/1997 | Leung et al. ........... 424/78.35 |
| 5,928,611 | 7/1999 | Leung ................... 422/131 |

FOREIGN PATENT DOCUMENTS

| | | |
|---|---|---|
| 57-70169 | 4/1982 | (JP) . |
| 57-70171 | 4/1982 | (JP) . |
| 3-126782 | 5/1991 | (JP) . |
| 3-296581 | 12/1991 | (JP) . |
| 4-8780 | 1/1992 | (JP) . |
| 4-9388 | 1/1992 | (JP) . |
| 4-146982 | 5/1992 | (JP) . |
| 6-100838 | 4/1994 | (JP) . |
| 6-122853 | 5/1994 | (JP) . |
| 6-240209 | 8/1994 | (JP) . |

\* cited by examiner

*Primary Examiner*—Thurman K. Page
*Assistant Examiner*—Sharon Howard
(74) *Attorney, Agent, or Firm*—Oliff & Berridge, PLC

(57) ABSTRACT

An adhesive composition that contains cyanoacrylate monomers and cyclic or alkyl- or phenyl-terminated linear polydimethylsiloxane is particularly useful in applications requiring flexibility and elasticity.

59 Claims, No Drawings

1,1-DISUBSTITUTED ETHYLENE ADHESIVE COMPOSITIONS CONTAINING POLYDIMETHYLSILOXANE

BACKGROUND

The invention relates to monomer and polymer adhesive and sealant compositions, and to their production and use for industrial and medical applications.

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

A concern in the use of adhesive compositions for treating wounds is the flexibility and elasticity of the cured adhesive, particularly in the face and body joint areas, such as hands, feet, elbows and knees.

Polymerized cyanoacrylate compositions are in general not flexible. Increased flexibility would improve the utility of cyanoacrylate compositions, particularly in body joint areas. Improved flexibility and elasticity would also make cyanoacrylate compositions better suited to use as drug delivery devices and the like under some circumstances.

Thus, a need exists for improved adhesive compositions, especially for medical uses, wherein the flexibility and elasticity of the adhesive is improved and the performance of the adhesive composition is not compromised. In particular, the need exists for a monomeric adhesive composition that possesses improved flexibility.

Polydimethylsiloxane (or PDMS) is a silicone compound that was developed for use as a dielectric coolant and in solar energy installations. However, it has also been used in other applications.

U.S. Pat. Nos. 4,477,607, 4,533,422 and Re. 32,889, all to Litke, disclose cyanoacrylate compositions that employ fumed silicas treated with polydimethylsiloxane or trialkoxyalkylsilane to improve the thixotropic properties of the compositions. Likewise, U.S. Pat. Nos. 4,764,545 and 4,686,247 to Yosida disclose an adhesive composition comprising an alpha cyanoacrylate and a silica surface-treated respectively with polydimethylsiloxane and with hexamethyldisilazane. Similarly, JP 06-122853 discloses an adhesive composition comprising an alpha cyanoacrylate and a hydrophobic silica surface-treated with dimethyldichlorosilane; U.S. Pat. No. 4,636,539 to Harris et al. discloses an adhesive comprising cyanoacrylate adhesive, fumed silica filler treated with polydialkylsiloxane, and calixarene compound; U.S. Pat. No. 4,180,911 to Bullock discloses a composition and method for use of a cyanoacrylate resin and a silane-treated inorganic powder in direct bonding of an orthodontic bracket structure to teeth and other dental applications; U.S. Pat. No. 4,713,405 to Koga et al. discloses an adhesive composition comprising an alpha cyanoacrylate and a fumed silica having a surface treated with a dimethyldichlorosilane and trialkyl borate; U.S. Pat. No. 5,373,035 to Uemura et al. discloses an adhesive composition comprising an alpha cyanoacrylate and a hydrophobic silica surface-treated with dimethyldichlorosilane; and U.S. Pat. No. 5,248,708 to Uemura et al. discloses an adhesive composition having a particular alpha cyanoacrylate, a fine silica and silanol group.

U.S. Pat. No. 5,214,093 to Nell et al. discloses an adhesive mixture for nonsurgical blepharoplasty. In the main embodiments, the base adhesive component is an oxygen permeable polysiloxane in a solvent. A less preferred embodiment includes a homogeneous mixture of cyanoacrylate adhesive and two separate miscible silicon oil components that are said to provide lubrication and breathability to the skin surface. These components are disclosed to be used in amounts of 50% cyanoacrylate, 25% polydimethylsiloxane and 25% 3-methacryloxy propyltris (trimethoxysiloxy) silane, and can be applied serially or in a mixture. The patent states that the mixture adheres in approximately five minutes and remains somewhat flexible during that time. It provides no further detail about the PDMS other than to indicate that it is "very oily and will penetrate the surface of the tissue to some extent." It is noted that silanes as a general matter raise toxicity issues, although this is not discussed in the Nell patent.

JP 57-70169, JP 57-70171, JP 03-126782, JP 03-296581, JP 04-146982 and JP 06-100838 disclose α-cyanoacrylate adhesive compositions containing specific organosilicon compounds including silicone oils and compounds related to PDMS. However, the disclosed compounds include various side and/or terminal groups that raise issues as to the stability and utility of the resultant compositions.

U.S. Pat. No. 4,906,317 to Liu discloses a cyanoacrylate adhesive composition which employs silacrown compounds as additives.

U.S. Pat. No. 4,837,260 to Sato et al. discloses an adhesive composition comprising an alpha cyanoacrylate and a hydrophobic silica along with particular curing accelerators.

U.S. Pat. No. 4,650,826 to Waniczek et al. discloses the use of silyl ester as a stabilizer for a cyanoacrylate adhesive.

U.S. Pat. No. 5,386,047 to Nakos et al. discloses a polymerizable composition comprising a monomer component, which includes a silicon containing di-alpha-cyanopentadienoate disiloxane compound. The monomer component further includes an alpha cyanoacrylate compound.

U.S. Pat. No. 4,705,836 to Ohtsuka et al. discloses a bonding composition including vinyl benzoic acid and cyanoacrylic acid ester. The composition further contains a silane compound.

U.S. Pat. No. 5,140,084 to Mikuni et al. discloses a silicone-containing alpha-cyanoacrylate that is useful as an adhesive. Similar silicone-containing alpha-cyanoacrylate compositions are also disclosed in JP 04-9388 and JP 04-8780.

SUMMARY OF THE INVENTION

The present invention provides a monomeric adhesive composition comprising a polymerizable 1,1-disubstituted ethylene adhesive monomer and a polydimethylsiloxane, which is alkyl, preferably methyl, or phenyl terminated or cyclic. The composition is free or substantially free of silane compounds. Production of the composition includes providing a mixture of the polymerizable monomer and polydimethylsiloxane in a container, and sealing the container, and optionally sterilizing the container and the mixture. The polydimethylsiloxane is preferably selected and provided in an amount such that it is soluble in the monomer at room temperature. The compositions produced, packaged and optionally sterilized according to the present invention are stable, and have extended utility. Compositions of the present invention have increased flexibility, elasticity, tissue (e.g., skin) wettability, stability, moisture vapor transmission rate, oxygen transmission rate, and/or scar tissue formation avoidance properties.

DETAILED DESCRIPTION OF EMBODIMENTS

According to the invention, a monomeric adhesive composition comprises at least one polymerizable 1,1-disubstituted ethylene monomer and at least one polydimethylsiloxane (PDMS), and is at least substantially free of silane compounds.

The polydimethylsiloxane suitable for use in the present invention can be alkyl- or phenyl-terminated linear or cyclic or a mixture thereof. Although not limited thereto, the PDMS used in the present invention is preferably a relatively short or small compound, as opposed to a long chain polymer. Thus, for example, the PDMS compound preferably has a low molecular weight, e.g., has a small number of monomer units, and also a low viscosity. The PDMS compound is selected such that it is compatible with the monomer (i.e., does not adversely affect polymerization, cure properties, or shelf-life). Preferably, the polydimethylsiloxane is soluble (i.e., dissolves) in the monomer composition at room temperature (i.e., 20–25° C.) so that it may be combined into the monomer composition without excessive heating of the monomer composition.

Solubility is preferred because a higher elongation effect can be provided by the agent upon polymerization of the adhesive composition when it is dispersed throughout the monomer composition in the form of a solution. In embodiments, the adhesive composition, including the polydimethylsiloxane, can provide an elongation at break of at least 100%, preferably 200–600%, 300–500% or 400–500%, of a polymerized film of the adhesive. If the polydimethylsiloxane is not in the form of a solution, then it is possible that it may settle or otherwise agglomerate, and thereby, upon subsequent polymerization of the composition, not provide the desired consistent elongation effect to the polymerized adhesive composition Thus, it is preferred in embodiments that the polydimethylsiloxane exhibits an at least substantially uniform concentration throughout the monomer composition. Where excess polydimethylsiloxane is added to the composition, i.e., an amount above the solubility point of the PDMS, it is acceptable that a portion of the PDMS remains undissolved in the composition so long as it does not act as two separate phases. Thus for example, in embodiments a stable microemulsion (with only microphases) may be acceptable.

The amount of polydimethylsiloxane that is added to the monomer composition can depend upon the selection of the specific PDMS and the specific monomer. For example, linear polydimethylsiloxane can often be included in a concentration of about 5–25 % by weight, preferably about 5–23% by weight, such as 10–15% by weight, of the adhesive composition relative to the total monomer and polydimethylsiloxane content. Cyclic polydimethylsiloxane can often be included in a concentration of about 5–50% by weight, preferably about 10–30% by weight, such as 10–15, 20 or 25% by weight of the adhesive composition. As noted above, however, contents above these ranges can also be used as desired. The amount of polydimethylsiloxane to be used can be determined by one of ordinary skill in the art using known techniques without undue experimentation in light of the present disclosure.

The polydimethylsiloxane preferably has a low weight average molecular weight. For example, suitable polydimethylsiloxanes preferably have a weight average molecular weight of from about 230 to about 1,500, more preferably from about 300 to about 1,000. Molecular weights outside of these ranges can also be used depending upon the specific polydimethylsiloxane and monomer composition so long as they are soluble or in a microemulsion in the adhesive composition as discussed above.

In exemplary embodiments, a linear polydimethylsiloxane averaging from two to ten, such as two to eight, for example, three, four, five or six monomer units, is preferred. One particularly preferred exemplary linear PDMS is a linear trimethylsiloxy terminated polydimethylsiloxane (TMDS) (CAS #9016-00-6), having a weight average molecular weight of 770, and a viscosity of about 5 centipoise at 25° C.

In other embodiments, the polydimethylsiloxane can be a cyclic polydimethylsiloxane. Such cyclic PDMS compounds are preferably also relatively small, having, for example, from two to ten, such as two to six, for example two to five monomer units. In an exemplary embodiment, a four monomer unit cyclic polydimethylsiloxane can be used. In embodiments, the cyclic PDMS can be selected from octamethylcyclotetrasiloxane (OMTS), decamethylcyclopentasiloxane (DMPS) and dodecamethylcyclohexasiloxane (DMHS). One exemplary cyclic PDMS is a product of United Chemical Technologies Inc. that has the formula $C_8H_{24}O_4Si_4$ (CAS #556-67-2) having a weight average molecular weight of 296.16, a density of 0.956 at 20° C. and a viscosity of about 2.3 centipoise at 25° C.

The linear PDMS is terminated with alkyl or phenyl groups. The linear or cyclic PDMS can optionally include or be free of alkyl side chain groups. Terminal and side chain groups can include, but are not limited to, alkyl groups with one to twelve, preferably 1–8 such as 1–6 or 1–4, carbon atoms, including for example methyl, ethyl or propyl groups.

Linear PDMS of the invention can be depicted by the formula:

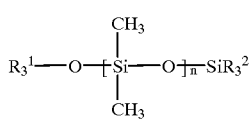

I wherein $R^1$ and $R^2$ are independently selected alkyl or phenyl groups. Cyclic PDMS of The invention can be depicted by the formula:

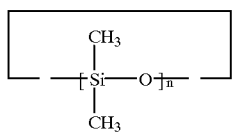

In each case, n is selected to provide the desired molecular weight. Thus n may be, for example, 2 or 3 to 12, preferably 4 to 10 or 4 to 8. One or more of the methyl groups may be alkyl substituted.

The polydimethylsiloxane for use in the present invention preferably has a low viscosity, such as from about 1 to about 15 centipoise at 25° C., as measured by a Brookfield Viscometer. More preferably, the polydimethylsiloxane has a viscosity of from about 2 to about 10 centipoise, such as from about 5 to about 7.5 centipoise at 25° C.

In embodiments, the polydimethylsiloxane is purified prior to mixing with the polymerizable monomer. A polydimethylsiloxane that is at least 98.5% by weight pure (i.e., containing 1.5% by weight or less impurities or ingredients other than polydimethylsiloxane) is preferred. Purification can be achieved, for example, by distillation.

A suitable procedure for selecting a polydimethylsiloxane involves selecting a group of potential polydimethylsiloxanes, assessing their solubility and stability in the monomer composition, and optionally testing for their compatibility with one or more sterilization procedures.

Potential polydimethylsiloxanes for testing can readily be selected by one of ordinary skill in the art from known sources in accordance with the disclosure herein. Once a potential agent is selected, it can be tested for solubility and stability in the monomer composition, such as by mixing an appropriate amount of the polydimethylsiloxane with a desired amount of the monomer composition and any other desired additives.

It is important to maintain the stability of the monomer composition within acceptable levels, such as commercially acceptable levels whereby the composition is not prematurely polymerized prior to application of the monomer composition to a desired substrate. One measure of the stability of the composition, other than a visual examination of the properties of the composition, is a measure of any changes in viscosity of the composition from a time prior to adding the polydimethylsiloxane to a time after adding the polydimethylsiloxane. For example, dramatic increases or decreases in viscosity can indicate instability of the composition, such as premature polymerization or other chemical degradation of the monomer composition or components thereof.

In embodiments of the present invention, it is preferred that the polydimethylsiloxane exhibit stability in the monomer composition for at least five minutes after mixing or dissolving the polydimethylsiloxane in the polymerizable monomer compound. More preferably, stability of the monomer composition is maintained for a time period sufficient to provide a commercially significant shelf-life to the monomer composition, such as 12, 18, or preferably 24 or more months. As used herein, "stability" refers to the composition maintaining a commercially acceptable form for the prescribed amount of time. That is, the composition does not prematurely polymerize or otherwise change form or degrade to the point that the composition is not useful for its intended purpose. Thus, while some polymerization or thickening of the composition may occur, such as can be measured by changes in viscosity of the composition, such change is not so extensive as to destroy or significantly impair the usefulness of the composition.

In embodiments, the adhesive composition has a viscosity of about 1–5000 centipoise, preferably 1–600 centipoise, more preferably 1–100 or 2–50 centipoise such as 2–18, 2–10 centipoise, or 30–500 such as 50–100 or 100–200 centipoise at 25° C. The viscosity can be select according to the proposed use—e.g., 1–100 centipoise for certain uses and 100–200 centipoise for other uses. Additionally, the composition may be a gel, e.g., 50,000–500,000 centipoise at 25° C. The viscosity of the adhesive composition can be measured with a Brookfield Viscometer. Additionally, in embodiments where a sterilization treatment is applied, the viscosity of the composition should preferably be maintained or increased by a controlled and acceptable amount after sterilization.

Compatibility of the polydimethylsiloxane-containing composition with one or more sterilization procedures is preferred in embodiments of the present invention because many uses of the polymerizable monomer compositions, such as many surgical and other medical applications, require sterilized products. In preferred embodiments, there is substantially no initiation of polymerization of monomeric liquid adhesive compositions that affects the utility of the monomer or monomers caused by the sterilization process.

Sterilization of the monomer composition and/or its packaging can be accomplished by techniques known to the skilled artisan, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retoit canning. Examples of irradiation methods include, but are not limited to, gamma irradiation, electron beam irradiation, and microwave irradiation. A preferred method is electron beam irradiation. In embodiments where a composition is to be used for medical applications, the sterilized composition must show low levels of toxicity to living tissue during its useful life.

The monomer (including prepolymeric) adhesive composition may include one or more polymerizable monomers. Preferred monomer compositions of the present invention, and polymers formed therefrom, are useful as tissue adhesives, sealants for preventing bleeding or for covering open wounds, and in other biomedical applications. They find uses in, for example, apposing surgically incised or traumatically lacerated tissues; retarding blood flow from wounds; dressing burns; dressing skin or other superficial or surface wounds such as compromised skin or other tissue (such as abrasions, chaffed or raw skin, minor cuts and scrapes, irritation, sores and/or stomatitis); protecting intact skin; and aiding repair and regrowth of living tissue. They are particularly useful for treating tissues that are subjected to flexing, such as faces and joints such as on hands, feet, elbows and knees. Monomer compositions of the present invention, and polymers formed therefrom, are also useful in industrial and home applications, for example in bonding rubbers, plastics, wood, composites, fabrics, and other natural and synthetic materials, particularly when applied at an area that is subjected to flexing.

Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade.

Such monomers are disclosed in, for example, U.S. Pat. No. 5,328,687 to Leung, et al., which is hereby incorporated in its entirety by reference herein.

Useful 1,1-disubstituted ethylene monomers include, but are not limited to, monomers of the formula:

$$HRC=CXY \qquad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include α-cyanoacrylates, vinylidene cyanides, C$_1$–C$_4$ alkyl homologues of vinylidene cyanides, dialkyl methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are α-cyanoacrylates. These monomers are known in the art and have the formula

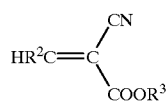
(II)

wherein R$^2$ is hydrogen and R$^3$ is a hydrocarbyl or substituted hydrocarbyl group; a group having the formula —R$^4$—O—R$^5$—O—R$^6$ or —R$^5$—O—R$^6$, wherein R$^4$ is a 1,2-alkylene group having 2–4 carbon atoms, R$^5$ is an alkylene group having 2–4 carbon atoms, and R$^6$ is an alkyl group having 1–6 carbon atoms; or a group having the formula

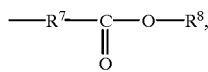

wherein R$^7$ is

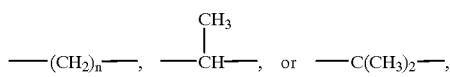

wherein n is 1–10, preferably 1–5, and R$^8$ is an organic moiety.

Examples of suitable hydrocarbyl and substituted hydrocarbyl groups include straight chain or branched chain alkyl groups having 1–16 carbon atoms; straight chain or branched chain C$_1$–C$_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety R$^8$ may be substituted or unsubstituted and may be straight chain, branched or cyclic, saturated, unsaturated or aromatic. Examples of such organic moieties include C$_1$–C$_8$ alkyl moieties, C$_2$–C$_8$ alkenyl moieties, C$_2$–C$_8$ alkynyl moieties, C$_3$–C$_{12}$ cycloaliphatic moieties, aryl moieties such as phenyl and substituted phenyl and aralkyl moieties such as benzyl, methylbenzyl, and phenylethyl. Other organic moieties include substituted hydrocarbon moieties, such as halo (e.g., chloro-, fluoro- and bromo-substituted hydrocarbons) and oxy-substituted hydrocarbon (e.g., alkoxy substituted hydrocarbons) moieties. Preferred organic radicals are alkyl, alkenyl, and alkynyl moieties having from 1 to about 8 carbon atoms, and halo-substituted derivatives thereof. Particularly preferred are alkyl moieties of 4 to 6 carbon atoms.

In the cyanoacrylate monomer of formula (II), R$^3$ is preferably an alkyl group having 1–10 carbon atoms or a group having the formula —AOR$^9$, wherein A is a divalent straight or branched chain alkylene or oxyalkylene moiety having 2–8 carbon atoms, and R$^9$ is a straight or branched alkyl moiety having 1–8 carbon atoms.

Examples of groups represented by the formula —AOR$^9$ include 1-methoxy-2-propyl, 2-butoxy ethyl, isopropoxy ethyl, 2-methoxy ethyl, and 2-ethoxy ethyl.

The α-cyanoacrylates of formula (II) can be prepared according to methods known in the art. U.S. Pat. Nos. 2,721,858 and 3,254,111, each of which is hereby incorporated in its entirety by reference, disclose methods for preparing α-cyanoacrylates. For example, the α-cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The α-cyanoacrylate monomers prepared with low moisture content and essentially free of impurities are preferred for biomedical use.

The α-cyanoacrylates of formula (II) wherein R$^3$ is a group having the formula R$^4$—O—R$^5$—O—R$^6$ or —R$^5$—O—R$^6$ can be prepared according to the method disclosed in U.S. Pat. No. 4,364,876 to Kimura et al., which is hereby incorporated in its entirety by reference. In the Kimura et al. method, the α-cyanoacrylates are prepared by producing a cyanoacetate by esterifying cyanoacetic acid with an alcohol or by transesterifying an alkyl cyanoacetate and an alcohol; condensing the cyanoacetate and formaldehyde or paraformaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The α-cyanoacrylates of formula (II) wherein R$^3$ is a group having the formula

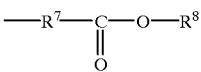

can be prepared according to the procedure described in U.S. Pat. No. 3,995,641 to Kronenthal et al., which is hereby incorporated in its entirety by reference. In the Kronenthal et al. method, such α-cyanoacrylate monomers are prepared by reacting an alkyl ester of an α-cyanoacrylic acid with a cyclic 1,3-diene to form a Diels-Alder adduct which is then subjected to alkaline hydrolysis followed by acidification to form the corresponding α-cyanoacrylic acid adduct. The α-cyanoacrylic acid adduct is preferably esterified by an alkyl bromoacetate to yield the corresponding carbalkoxymethyl α-cyanoacrylate adduct. Alternatively, the α-cyanoacrylic acid adduct may be converted to the α-cyanoacrylyl halide adduct by reaction with thionyl chloride. The α-cyanoacrylyl halide adduct is then reacted with an alkyl hydroxyacetate or a methyl substituted alkyl hydroxyacetate to yield the corresponding carbalkoxymethyl α-cyanoacrylate adduct or carbalkoxy alkyl α-cyanoacrylate adduct, respectively. The cyclic 1,3-diene blocking group is finally removed and the carbalkoxy methyl α-cyanoacrylate adduct or the carbalkoxy alkyl α-cyanoacrylate adduct is converted into the corresponding carbalkoxy alkyl α-cyanoacrylate by heating the adduct in the presence of a slight deficit of maleic anhydride.

Examples of monomers of formula (I) include cyanopentadienoates and α-cyanoacrylates of the formula:

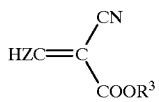

(III)

wherein Z is —CH═CH, and R$^3$ is as defined above. The monomers of formula (III) wherein R$^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated in its entirety by reference.

Preferred α-cyanoacrylate monomers used in this invention are alkyl α-cyanoacrylates including octyl cyanoacrylate, such as 2-octyl cyanoacrylate; dodecyl cyanoacrylate; 2-ethylhexyl cyanoacrylate; butyl cyanoacrylate such as n-butyl, iso-butyl or tert-butyl cyanoacrylate; ethyl cyanoacrylate; methyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. More preferred monomers are n-butyl and 2-octyl α-cyanoacrylate. Monomers utilized for medical purposes in the present application should be very pure and contain few impurities (e.g., surgical grade). Monomers utilized for industrial purposes need not be as pure.

The composition may optionally also include at least one other plasticizing agent that assists in imparting flexibility to the polymer formed from the monomer. The plasticizing agent preferably contains little or no moisture and should not significantly affect the stability or polymerization of the monomer.

Examples of suitable plasticizers include tributyl citrate, acetyl tri-n-butyl citrate (ATBC), dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myiistate, butyl stearate, lauric acid, trioctyl trimellitate, dioctyl glutarate, and mixtures thereof Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates. Some thickeners, such as poly-2-ethylhexylcyanoacrylate, can also impart flexibility to the polymer. Polymethyl methacrylate (PMMA) and hexadimethylsilazane (HDMS) are particularly useful as plasticizers in high viscosity (e.g., greater than 100 centipoise at 25° C.) formulations containing PDMS, while tributyl citrate and acetyl tributyl citrate are particularly useful as plasticizers in low viscosity (e.g., less than 50 centipoise at 25° C.) formulations containing PDMS.

The addition of other plasticizing agents, in addition to the polydimethylsiloxane, in amounts ranging from about 0.5 wt. % to about 25 wt. %, or from about 1 wt. % to about 20 wt. %, or from about 3 wt. % to about 15 wt. % or from about 4 wt. % to about 6 wt. %, based on the entire composition, may further increase elongation and toughness of the polymerized monomer over polymerized monomers not having the additional plasticizing agents.

The composition may also optionally include at least one thixotropic agent. Suitable thixotropic agents are known to the skilled artisan and include, but are not limited to, silica gels such as those treated with a silyl isocyanate, and optionally surface treated titanium dioxide. However, in some embodiments, the adhesive composition contains no, or substantially no, silica. Examples of suitable thixotropic agents and thickeners are disclosed in, for example, U.S. Pat. No. 4,720,513, and U.S. patent application Ser. No. 09/374,207 filed Aug. 12, 1999, the entire disclosures of which are hereby incorporated in their entirety.

The thickening agents may be selected from among known thickeners, including, but not limited to, poly(2-ethylhexyl methacrylate), poly(2-ethylhexyl acrylate) and celluose acetate butyrate. Suitable thickeners include, for example, polycyanoacrylates, polyoxalates, lactic-glycolic acid copolymers, polycaprolactone, lactic acid-caprolactone copolymers, poly(caprolactone+DL-lactide+glycolide), polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(butylmethacrylate) and poly(butylacrylate), also copolymers of various acrylate and methacrylate monomers, such as poly(butylmethacrylate-co-methylmethacrylate). Biodegradable polymer thickeners are preferred for some uses such as some surgical uses. Preferably, the thickening agent is soluble in a monomer composition at room temperature (i.e., 20–25° C.) so that it may be added to the monomer composition without excessive heating of the monomer composition and remain uniformly combined in the composition.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The composition may also optionally include one or more stabilizers, preferably both at least one anionic vapor phase stabilizer and at least one anionic liquid phase stabilizer. These stabilizing agents inhibit premature polymerization. Such stabilizing agents may also include mixtures of anionic stabilizing agents and radical stabilizing agents such as hydroquinone, p-methoxyphenol and butylated hydroxyanisole (BHA). Any mixture of stabilizers is included as long as the mixture does not inhibit the desired polymerization of the monomer.

The anionic vapor phase stabilizers may be selected from among known stabilizers, including, but not limited to, sulfur dioxide, boron trifluoride, and hydrogen fluoride. The amount of anionic vapor phase stabilizer that is added to the monomer composition depends on the identity of the liquid phase stabilizer(s) chosen in combination with it, the monomer to be stabilized, as well as the packaging material to be used for the composition. Preferably, each anionic vapor phase stabilizer is added to give a concentration of less than 200 parts per million (ppm). In preferred embodiments, each anionic vapor phase stabilizer is present from about 1 to 200 ppm, more preferably from about 10 to 75 ppm, even more preferably from about 10 to 50 ppm, and most preferably from 10 to 20 ppm. The amount to be used can be determined by one of ordinary skill in the art using known techniques without undue experimentation.

In embodiments, the vapor phase comprises, among other things, an anionic stabilizer that is sulfur dioxide. In embodiments, the vapor phase comprises, among other things, a stabilizer that is boron trifluoride or hydrogen fluoride. A combination of sulfur dioxide and boron trifluoride or hydrogen fluoride is preferable in some embodiments.

In embodiments, the liquid phase anionic stabilizer is a very strong acid. As used herein, a very strong acid is an acid that has an aqueous $pK_a$ of less than 1.0. Suitable very strong acidic stabilizing agents include, but are not limited to, very strong mineral and/or oxygenated acids. Examples of such very strong acids include, but are not limited to, sulfuric acid ($pK_a$–3.0), perchloric acid ($pK_a$–5), hydrochloric acid ($pK_a$–7.0), hydrobromic acid ($pK_a$–9), fluorosulfonic acid ($p_{Ka}$<–10), chlorosulfonic acid ($pK_a$–10). In embodiments, the very strong acid liquid phase anionic stabilizer is added to give a final concentration of 1 to 200 ppm. Preferably, the very strong acid liquid phase anionic stabilizer is present in a concentration of from about 5 to 80 ppm, more preferably 10 to 40 ppm. The amount of very strong acid liquid phase anionic stabilizer to be used can be determined by one of ordinary skill in the art without undue experimentation.

Preferably, the very strong acid liquid phase anionic stabilizer is sulfuric acid, perchloric acid, or chlorosulfonic acid. More preferably, the very strong acid liquid phase anionic stabilizer is sulfuric acid.

In embodiments, sulfur dioxide is used as a vapor phase anionic stabilizer and sulfuric acid is used as a liquid phase anionic stabilizer.

The composition may also optionally include at least one other anionic stabilizing agent that inhibits premature polymerization. These agents are herein referred to as secondary anionic active agents to contrast them with the strong or very strong liquid phase anionic stabilizers, which are referred to hereinbelow as "primary" anionic stabilizers. The secondary anionic active agents can be included in the compositions to adjust the cure speed of the adhesive composition, for example.

The secondary anionic active agent would normally be an acid with a higher $pK_a$ than the primary anionic stabilizing agent and may be provided to more precisely control the cure speed and stability of the adhesive, as well as the molecular weight of the cured adhesive. Any mixture of primary anionic stabilizers and secondary active agents is included as long as the chemistry of the composition is not compromised and the mixture does not significantly inhibit the desired polymerization of the composition. Furthermore, the mixture should not, in medical adhesive compositions, show unacceptable levels of toxicity.

Suitable secondary anionic active agents include those having aqueous $pK_a$ ionization constants ranging from 2 to 8, preferably from 2 to 6, and most preferably from 2 to 5. Examples of such suitable secondary anionic stabilizing agents include, but are not limited to, phosphoric acid ($pK_a$ 2.2), organic acids, such as acetic acid ($pK_a$ 4.8), benzoic acid ($pK_a$ 4.2), chloroacetic acid ($pK_a$ 2.9), cyanoacetic acid, and mixtures thereof. Preferably these secondary anionic stabilizing agents are organic acids, such as acetic acid or benzoic acid. In embodiments, the amount of acetic acid and/or benzoic acid is about 25–500 ppm. The concentration of acetic acid is typically 50–400 ppm, preferably 75–300 ppm, and more preferably 100–200 ppm. When using a stronger acid such as phosphoric acid, a concentration of 20–100 ppm, preferably 30–80 ppm, and more preferably 40–60 ppm may be utilized.

Combinations of at least one vapor phase stabilizer and at least one liquid phase anionic stabilizer are preferred. For example, combinations of sulfur dioxide and sulfuric acid; sulfur dioxide and perchloric acid; sulfur dioxide and chlorosulfonic acid; boron trifluoride and sulfuric acid; boron trifluoride and perchloric acid; boron trifluoride and chlorosulfonic acid; boron trifluoride and methanesulfonic acid; hydrogen fluoride and sulfuric acid; hydrogen fluoride and perchloric acid; hydrogen fluoride and chlorosulfonic acid; hydrogen fluoride and methanesulfonic acid; boron trifluoride, sulfur dioxide, and sulfuric acid; sulfur dioxide, sulfuric acid and acetic acid; and other combinations can be used. The two types of anionic stabilizers are chosen in conjunction such that the stabilizers are compatible with the chosen adhesive composition and each other, as well as with the packaging material and the equipment used to make and package the composition. In other words, the combination of vapor phase stabilizer(s), liquid phase stabilizer(s), radical stabilizers and monomer should be such that a stabilized, substantially unpolymerized adhesive composition is present after packaging.

It has been found, however, that compositions of the invention can require less stabilizer than corresponding compositions without the PDMS.

The stability, and thus the shelf-life, of some monomeric adhesive compositions can be further enhanced and extended through careful regulation of the packaging. Treated (e.g., fluorinated polymer) packaging such as that disclosed in copending U.S. patent application No. (100497.02) filed Oct. 29, 1999, which is hereby incorporated by reference in its entirety, is preferred and may reduce the amount of stabilizer that is combined into the composition.

The compositions may also include pH modifiers to control the rate of degradation of the resulting polymer, as disclosed in U.S. patent application No. 08/714,288, filed Sep. 18, 1996, the entire disclosure of which is hereby incorporated by reference.

Medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitrites; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al., which are hereby incorporated by reference in their entireties.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such cross-linking agents. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoaciylates). A catalytic amount of an amine activated free radical initiator or rate modifier may be added to initiate polymerization or to modify the rate of polymerization of the cyanoacrylate monomer/crosslinking agent blend.

In embodiments of the present invention, the composition and/or its applicator may contain materials such as a polymerization initiator, accelerator, rate-modifier, flavorant, and/or cross-linking agent for initiating polymerization and/or cross-linking of the polymerizable monomer material. Suitable materials and applicators and packaging systems are disclosed in U.S. Pat. No. 5,928,611 and U.S. patent applications Ser. Nos. 09/430,177, 09/430,176, 09/430,289, 09/430,290, and 09/430,180 filed Oct. 29, 1999; Ser. No. 09/343,914 filed Jun. 30, 1999; Ser. No. 09/385,030 filed Aug. 30, 1999; and Ser. No. 09/176,889 filed Oct. 22, 1998; the entire disclosures of which are incorporated herein by reference. A preferred initiator for some uses, especially industrial uses, is dimethyl toluidine.

The compositions of this invention may further contain fibrous reinforcement and colorants such as dyes, pigments, and pigment dyes. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphenoyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)]copper.

The compositions of this invention may further contain preservatives. In embodiments, the preservatives may be selected from among known preservatives including, but not limited to, parabens and cresols. For example, suitable parabens include, but are not limited to, alkyl parabens and salts thereof, such as methylparaben, methylparaben sodium, ethylparaben, propylparaben, propylparaben sodium, butylparaben, and the like. Suitable cresols include, but are not limited to, cresol, chlorocresol, and the like. The preservatives can also be selected from other known agents including, but not limited to, hydroquinone, pyrocatechol, resorcinol, 4-n-hexyl resorcinol, captan (i.e., 3a,4,7,7a-tetrahydro-2-((trichloromethyl)thio)-1H-isoindole-1,3(2H)-dione), methyl-4-hydroxybenzoate, benzalkonium chloride, benzalkonium chloride solution, benzethonium chloride, benzoic acid, benzyl alcohol, butylated hydroxy-anisole (BHA), cetylpyridinium chloride, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercuric nitrate and phenylmercuric acetate, formaldehyde, and formaldehyde generators such as the preservatives Germall II® and Germall 115® (imidazolidinyl urea, available from Sutton Laboratories, Charthan, N.J.). In embodiments, mixtures of two or more preservatives can also be used. See also U.S. patent application Ser. No. 09/430,180 filed Oct. 29, 1999, which is hereby incorporated herein in its entirety by reference.

EXAMPLES

Examples of formulations of the invention are presented in the following Table I in which the α-cyanoacrylate monomer is stabilized with anionic and radical stabilizers, and the composition includes a colorant, 0.5% or less of each of methyl paraben and BHA as preservatives, and is packaged in a post-fluorinated HDPE container.

TABLE I

| | Compositions | |
|---|---|---|
| Stabilized Monomer (Wt %) | PDMS (Wt %) | Plasticizer (Wt %) |
| n-butyl CA (75) | TMDS (20) | PEG (5) |
| n-butyl CA (75) | TMDS (25) | — |
| n-butyl CA (75) | OMTS (20) | ATBC (5) |
| n-butyl CA (75) | OMTS (25) | — |
| n-butyl CA (75) | DMPS (20) | PMMA (5) |
| n-butyl CA (75) | DMPS (25) | — |
| n-butyl CA (75) | DMHS (20) | HDMS (5) |
| n-butyl CA (75) | DMHS (25) | — |
| 2-octyl CA (75) | TMDS (20) | PEG (5) |
| 2-octyl CA (75) | TMDS (25) | — |
| 2-octyl CA (75) | OMTS (20) | ATBC (5) |
| 2-octyl CA (75) | OMTS (25) | — |
| 2-octyl CA (75) | DMPS (20) | PMMA (5) |
| 2-octyl CA (75) | DMPS (25) | — |
| 2-octyl CA (75) | DMHS (20) | HDMS (5) |
| 2-octyl CA (75) | DMHS (25) | — |

EXPERIMENTAL RESULTS

TABLE II

Elongation of 2-Octyl Cyanoacrylate Film

| Sample | Peak Stress (psi) | Elongation at Break (inches) | Modulus (psi) |
|---|---|---|---|
| 0% OMTS | 1370 +/− 41 | 3.1 +/− 1.6 | 18624 +/− 703 |
| 2% OMTS | 1035 +/− 77 | 7.0 +/− 1.5 | 12343 +/− 502 |
| 10% OMTS | 686 +/− 95 | 10.5 +/− 1.4 | 5753 +/− 353 |
| 20% OMTS | 441 +/− 65 | 11.3 +/− 2.0 | 3189 +/− 316 |

Film tensile properties were tested using a MTS Sintech 2/G mechanical testing machine with TestWorks software version 3.08. The procedure used for this determination is a modified version of ASTM D882-95a (Standard Test Method for Tensile Properties of Thin Plastic Shecting). A 10 1bf load cell was used to determine these properties with a constant crosshead speed of 3.0 inches/minute. Small pneumatic grips were used to clamp the film on each end. The size of the films was 4 inches×0.5 inches with variance in thickness. A gage length of 3 inches was used, allowing 0.5 inches of each end of the film to be secured in the grips. Elongation at break, peak stress and modulus were calculated using this procedure.

This table demonstrates improved elasticity and elongation that may be achieved by way of the invention.

TABLE III

Solubilities of TMDS and OMTS in 2-Octyl Cyanoacrylate

| % PDMS | TMDS solutions | TMDS films | OMTS solutions | OMTS films |
|---|---|---|---|---|
| 0 | Clear | Clear | Clear | Clear |
| 2 | Clear | Clear | Clear | Clear |
| 5 | Clear | Clear | Clear | Clear |
| 10 | Slightly Cloudy | Clear | Clear | Clear |
| 15 | Slightly Cloudy | Clear | Clear | Clear |
| 20 | Cloudy | Cloudy | Clear | Clear |

This table demonstrates higher levels of soluble PDMS achievable by way of cyclic PDMS embodiments of the invention.

While the invention has been described with reference to preferred embodiments, the invention is not limited to the specific examples given, and other embodiments and modifications can be made by those skilled in the art without departing from the spirit and scope of the invention.

What is claimed is:

1. An adhesive composition, comprising polydimethylsiloxane and polymerizable 1,1-disubstituted ethylene adhesive monomer; wherein said composition is substantially free of silanes, said polydimethylsiloxane is dissolved in, or in a microemulsion in, said monomer; said polydimethylsiloxane is cyclic, or alkyl- or phenyl-terminated linear, polydimethylsiloxane; and said polydimethylsiloxane is optionally alkyl substituted.

2. The composition of claim 1, wherein said monomer is α-cyanoacrylate monomer.

3. The composition of claim 1, wherein said monomer is alkyl α-cyanoacrylate monomer.

4. The composition of claim 1, wherein said monomer comprises at least one member selected from the group consisting of ethyl cyanoacrylate, butyl cyanoacrylate, and 2-octyl cyanoacrylate.

5. The composition of claim 1, wherein said polydimethylsiloxane is linear.

6. The composition of claim 5, wherein said polydimethylsiloxane has an average of about 2–12 monomer units.

7. The composition of claim 5, wherein said polydimethylsiloxane has an average of about 3–4 monomer units.

8. The composition of claim 1, wherein said polydimethylsiloxane is linear trimethylsiloxy terminated polydimethylsiloxane.

9. The composition of claim 1, wherein said polydimethylsiloxane has a weight average molecular weight of from about 150 to about 1500.

10. The composition of claim 5, wherein said polydimethylsiloxane has a viscosity of less than 8 centipoise at 25° C.

11. The composition of claim 1, wherein said polydimethylsiloxane is cyclic.

12. The composition of claim 11, wherein said polydimethylsiloxane has an average of about 3–12 monomer units.

13. The composition of claim 1, wherein said polydimethylsiloxane is at least one member selected from the group consisting of octamethylcyclotetrasiloxane, decamethylcyclopentasiloxane and dodecamethylcyclohexasiloxane.

14. The composition of claim 1, wherein said polydimethylsiloxane is present in the composition in an amount of between about 5% and about 30% by weight relative to the total monomer and polydimethylsiloxane content.

15. The composition of claim 14, wherein said amount is between about 10% and about 25% by weight.

16. The composition of claim 14, wherein said amount is about 10–20% by weight.

17. The composition of claim 5, wherein said polydimethylsiloxane is alkyl-terminated.

18. The composition of claim 5, wherein said polydimethylsiloxane has methyl, ethyl or propyl terminal groups.

19. The composition of claim 5, wherein said polydimethylsiloxane is methyl terminated.

20. The composition of claim 1, wherein said polydimethylsiloxane is unsubstituted.

21. The composition of claim 1, wherein said composition is free of silica.

22. The composition of claim 1, wherein said composition further comprises at least one stabilizing agent.

23. The composition of claim 1, further comprising at least one plasticizer different from said polydimethylsiloxane.

24. The composition of claim 23, wherein said plasticizer is selected from the group consisting of tributyl citrate, acetyl tributyl citrate, polymethylmethacrylate and hexadimethylsilazane.

25. The composition of claim 23, wherein a viscosity of said composition is at least 100 centipoise at 25° C. and said plasticizer is at least one member selected from the group consisting of polymethylmethacrylate and hexadimethylsilazane.

26. The composition of claim 1, further comprising at least one antimicrobial preservative selected from the group consisting of cresols and parabens.

27. The composition of claim 1, wherein said composition is sterile.

28. The composition of claim 1, packaged in a post-fluorinated polymeric container.

29. A method of making the composition of claim 1, comprising dissolving a polydimethylsiloxane in a polymerizable 1,1-disubstituted ethylene adhesive monomer to form a solution.

30. The method of claim 29, wherein the polydimethylsiloxane is at least 98.5% by weight pure prior to said mixing.

31. The method of claim 29, wherein the polydimethylsiloxane is cyclic.

32. The method of claim 29, further comprising sterilizing said solution.

33. An adhesive composition comprising a polymerizable 1,1-disubstituted ethylene adhesive monomer and a cyclic polydimethylsiloxane.

34. The composition of claim 33, wherein said monomer is α-cyanoacrylate monomer.

35. The composition of claim 33, wherein said monomer is alkyl α-cyanoacrylate monomer.

36. The composition of claim 33, wherein said monomer comprises at least one member selected from the group consisting of ethyl cyanoacrylate, butyl cyanoacrylate, and 2-octyl cyanoacrylate.

37. The composition of claim 33, wherein said polydimethylsiloxane is at least one member selected from the group consisting of octamethylcyclotetrasiloxane, decamethylcyclopentasiloxane and dodecamethylcyclohexasiloxane.

38. The composition of claim 33, wherein the cyclic polydimethylsiloxane has a viscosity of about 5–7.5 centipoise at 25° C.

39. An adhesive composition comprising:

| | |
|---|---|
| (a) 2-alkyl cyanoacrylate | 65–90 wt %; |
| (b) cyclic polydimethylsiloxane | 10–35 wt %; |
| (c) plasticizer | 0–10 wt %; |
| (d) anionic stabilizer | 0–1 wt %; |
| (e) radical stabilizer | 0–1 wt %; |
| (f) antimicrobial preservative | 0–1 wt %; and |
| (g) colorant | 0–0.01 wt %. |

40. The composition of claim 39, wherein said alkyl cyanoacrylate is 2-octyl cyanoacrylate and said cyclic polydimethylsiloxane is octamethyltetracyclosiloxane.

41. The composition of claim 40, wherein said plasticizer is selected from the group consisting of polymethylmethacrylate, hexadimethylsilazane, tributyl citrate and acetyl tributyl citrate.

42. The composition of claim 40, wherein said preservative is methyl paraben.

43. A method of making a sterile composition comprising:
placing a mixture of a polymerizable cyanoacrylate monomer and a polydimethylsiloxane in a container, sealing said container, and sterilizing the mixture in the container.

44. The method of claim 43, wherein said polydimethylsiloxane is cyclic.

45. The method of claim 43, wherein said polydimethylsiloxane is selected from the group consisting of octamethylcyclotetrasiloxane, decamethylcyclopentasiloxane and dodecamethylcyclohexasiloxane.

46. The method of claim 43, wherein said sterilizing is performed by dry heat, moist heat, retort canning, gamma irradiation, electron beam irradiation, or microwave irradiation.

47. The method of claim 43, wherein said sterilizing is performed by electron beam irradiation.

48. A method of treating tissue, comprising applying the composition of claim 1 to said tissue.

49. The method of claim 48, wherein said tissue is at or adjacent a joint of a mammal.

50. The method of claim 49, wherein said joint is a human knee or elbow.

51. The method of claim 49, wherein said joint is on a human hand or foot.

52. The method of claim 48, wherein said tissue is on a human face.

53. The method of claim 48, wherein said monomer is 2-octyl cyanoacrylate and said polydimethylsiloxane is cyclic.

54. The method of claim 48, wherein said tissue is compromised.

55. The method of claim 54, wherein said tissue is burned, lacerated, irritated, abraded or incised.

56. The method of claim 48, wherein said tissue is skin.

57. The method of claim 56, wherein said skin is compromised.

58. The method of claim 56, wherein said skin is intact.

59. A polymer film formed by polymerizing the monomer of a film of an adhesive composition according to claim 1.

* * * * *